US005109860A

United States Patent [19]

Gelly et al.

[11] Patent Number: 5,109,860

[45] Date of Patent: May 5, 1992

[54] PROBE WITH CURVED BAR FOR AN ECHOGRAPH

[75] Inventors: Jean-François Gelly, Valbonne; Patrick Dubut, Tourrettes S/Loup; René Reynier, Cagnes S/Mer; Charles Maerfeld, Antibes, all of France

[73] Assignee: General Electric CGR SA, Issy Les Moulineaux, France

[21] Appl. No.: 368,338

[22] PCT Filed: Nov. 24, 1987

[86] PCT No.: PCT/FR87/00463

§ 371 Date: Jul. 17, 1989

§ 102(e) Date: Jul. 17, 1989

[87] PCT Pub. No.: WO88/04088

PCT Pub. Date: Jun. 2, 1988

[30] Foreign Application Priority Data

Nov. 28, 1986 [FR] France ................................ 86 16661

[51] Int. Cl.[5] ................................................ A61B 8/00

[52] U.S. Cl. .............................. 128/662.03; 29/25.35; 310/330

[58] Field of Search ....................................... 29/25.35; 178/662.03-662.06; 310/336, 337

[56] References Cited

U.S. PATENT DOCUMENTS 4,354,501 10/1982 Colley et al. ................... 128/662.06

4,556,066 12/1985 Semrow ......................... 128/662.03

FOREIGN PATENT DOCUMENTS 0128049 12/1984 European Pat. Off. .

2926182 1/1981 Fed. Rep. of Germany .

OTHER PUBLICATIONS

Patent Abstracts of Japan, vol. 7, No. 27 (E-156) (1172), Feb. 3, 1983 & JP, A, 57181299 (Yokogawa Denki Seisakusho K.K.), Nov. 8, 1982.

Patent Abstracts of Japan, vol. 7, No. 229 (E-203) (1374), Oct. 12, 1983, & JP, A, 58120397 (Hitachi Medeiko K.K.) Jul. 18, 1983.

*Primary Examiner*—Francis Jaworski

*Attorney, Agent, or Firm*—Oblon, Spivak, McClelland, Maier & Neustadt

[57] ABSTRACT

A curved bar probe (1) for an echograph is fabricated by using a thin support (2) on which is placed a bar of piezoelectric crystal. The bar is divided into a plurality of piezoelectric transducers elements (3). The thin support presents the particularity of being rigid at room temperature but is thermodeformable. By subjecting it to a heating-cooling cycle during which it is given a desired curved shape, a rigid bar having an imposed curved shape is obtained. It is then possible to avoid the adhesion of said support to a base (16). This would form a back-reflecting surface for acoustic waves and would create interference harmful to the useful acoustic signal.

10 Claims, 1 Drawing Sheet

PROBE WITH CURVED BAR FOR AN ECHOGRAPH

BACKGROUND OF THE INVENTION

1. Field of the Invention

An object of the present invention is a curved bar probe for an echograph. It finds application more particularly in the medical field where echographs are used for diagnostic purposes to reveal pictures of internal tissue structures of human bodies examined. Nevertheless it can be applied in all fields of utilization of ultrasound, or where curved bars are used.

2. Discussion of Background

An echograph schematically comprises electrical generating means to produce an electrical signal that vibrates at an acoustic frequency. This signal is applied to an element or, rather, to a bar of piezoelectric transducer elements where it is converted into a mechanical excitation. The probe emits this mechanical excitation in a medium against which it is placed. Outside periods of transmission, the probe may be used to receive acoustic signals back-reflected by the medium and to convert these acoustic signals into electrical signals which can be introduced into reception elements. From the electrical signal thus received, it is possible to extract useful information, notably information capable of enabling the creation of an image. The quality of the image depends on the way in which the medium to be examined is explored.

Among the various possible solutions, exploration by sector scanning is presently one of the most efficient ones. To obtain it, it is enough to excite a group of adjacent elements in the bar, with predetermined delays with respect to one another, so as to focus the acoustic wave in one direction at transmission (the same organization of the delays is planned at reception to favour a signal coming from a given direction). By modifying the composition of the group of elements, by interrupting, for example, the supply to an element located on one side of the set, and by putting another element located on the other side into operation, and by re-organizing the delays for the new group thus formed, a new direction is obtained for the focusing of the acoustic signals. If all the piezoelectric elements are aligned with one another along a straight line, the scanning of the examined medium is a scanning by translation. On the contrary, if the bar of elements is curved, the scanning follows the perpendicular to the tangent to the curve formed by the arrangement of the elements: it is sectorial if this curve is an arc of a circle.

The making of curved bar probes is conventionally done in the following way. A support is used, with a relatively small thickness, for example 2 to 3 mm, and made of a flexible material. Then, a small bar of piezoelectric crystal is fixed to this support. By cutting out operations, in particular with a saw, a partition is made in this small bar, so as to divide it into several piezoelectric elements. The partition is done in such a way that, between each element, the support is not cut. Each element remains fixed to the support. Since the support is flexible, it is then enough to fix it to a base with an appropriate curved shape to obtain a desired curved bar. In a European patent application No. 84 308 373.4, filed on Dec. 3, 1984, an embodiment of this type is described.

This approach, however, has a drawback. In effect, owing to the elastic nature of the support, it cannot be kept curved except by exerting a permanent holding force. As indicated by the document referred to, this force can be obtained by bonding the support to the base. The face of the piezoelectrical elements in front of the place where the useful acoustic waves are propagated, is called the front face, the face opposite the front face is called the rear face. During transmission, the transmitted acoustic wave is propagated, in principle, in both directions: frontwards and rearwards. Only the wave transmitted frontwards is useful. Steps are taken, accordingly, to prevent the disturbances due to the rear wave. In particular, action is taken on the acoustic impedance of the support and the base to prevent the rear wave from being reflected towards the bar. Now, this can be achieved only imperfectly once the support has a bonding surface on the base. This bonding surface reacts all the more strongly as the support is thin so as to be capable of being deformed and, hence, as this surface is close to the piezoelectric small bar proper.

Despite changes in the composition of the bonder used to join the support to its base, as indicated in the document referred to, the most efficient result is not obtained. Furthermore, the bonding operations are never perfect, and the solidness of the unit may be thereby affected. Finally, the very nature of the flexible elements used to this end is not favourable to the choice, for the material of the support, of good acoustic impedance. For, there are known ways of bringing the acoustical impedance of materials into by making mixtures or by including therein micro-beads made of plastic or glass for example. And flexible synthetic materials are ill-suited to this operation.

The characteristics of the introduction of claim 1 are known from the Japanese abstract 57181299. From the document EP-A-128 049, the making of a probe comprising the material, polymerizable epoxy resin, is known. The backing known from this document is bonded to the probe by a layer.

The probe according to the invention is characterized by the characteristics of the characterizing part of claim 1. The use of a probe of this type, comprising a cold polymerizable resin, enables the resolving of the problem of subsequently positioning the base (by the intimate adhesion of the two resins) without this positioning forming an echo surface for the rear acoustic wave.

BRIEF DESCRIPTION OF THE DRAWINGS

The invention will be better understood from the reading of following description and from an examination of the accompanying figures. These are given purely by way of indication and in no way restrict the scope of the invention. In the figures, the same references designate the same elements. These figures show.

DESCRIPTION OF THE PREFERRED EMBODIMENTS

Figure 1:
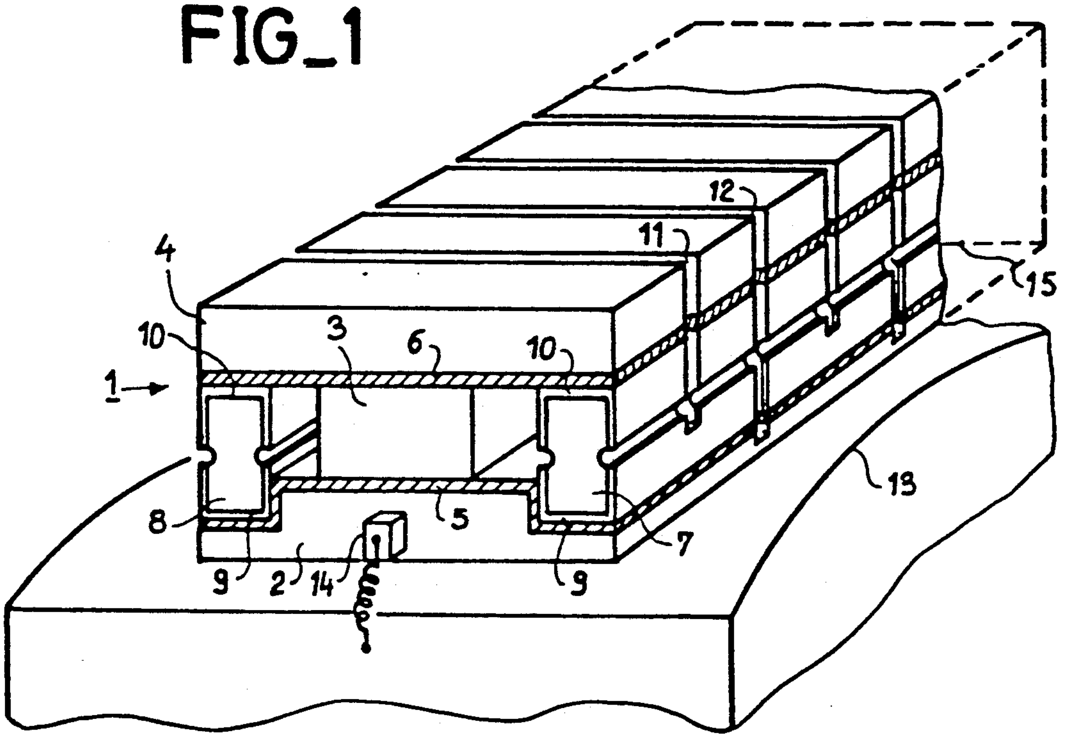
FIG. 1: a bar of piezoelectric elements mounted on a support according to the invention.

FIG. 1 shows a bar of piezoelectric transducer elements mounted on a support according to the invention. This bar 1 essentially has a support 2, piezoelectric elements such as 3, these piezoelectric elements being held between the support 2 and acoustic transition blades 4. Between the support 2 and each of the elements 3, there is an electrode 5, and between each of the elements 3 and each of the blades 4, there is an electrode 6. These electrodes are designed to receive an electrical signal at the time of an excitation. They then apply a corresponding electrical field to the element 3. Under the effect of this field, the element 3 starts vibrating and transmits, through the blade 4, the vibration to a medium which is to be studied and which is in contact with it (not shown). In a preferred embodiment, the electrical continuity of the electrodes 5 and 6 is carried on by blocks such as 7 and 8 placed on either side of each element. Each block made of an insulating material is covered with two electrically independent metallizations, 9 and 10 respectively, in each case in contact with the electrodes 5 and 6. These metallizations enable a simpler connection with the electrodes 5 and 6.

Apart from the presence of the blocks 7 and 8, the bar 1 is fabricated in the rectilinear state as in the prior art referred to. To build it, an elongated support 2, a rod made of piezoelectric material and an elongated blade are used: the support and the blade are bonded to the rod. For the improvement in connection referred to, during the assembly, strips already including the partition of the metallizations are inserted on either side of the rod. When this set is formed, cuts such as 11 and 12 are made, in general with a saw, to divide the piezoelectric rod into a series of independent piezoelectric elements. The support is only partly penetrated by these cuts: it ensures the cohesion of all the elements. There are known ways of preventing risks of diaphony between adjacent piezoelectric elements to provide each piezoelectric element (separated from one another by deep cuts 12) by shallower cuts 11 which cut them in their middle.

Figure 2:
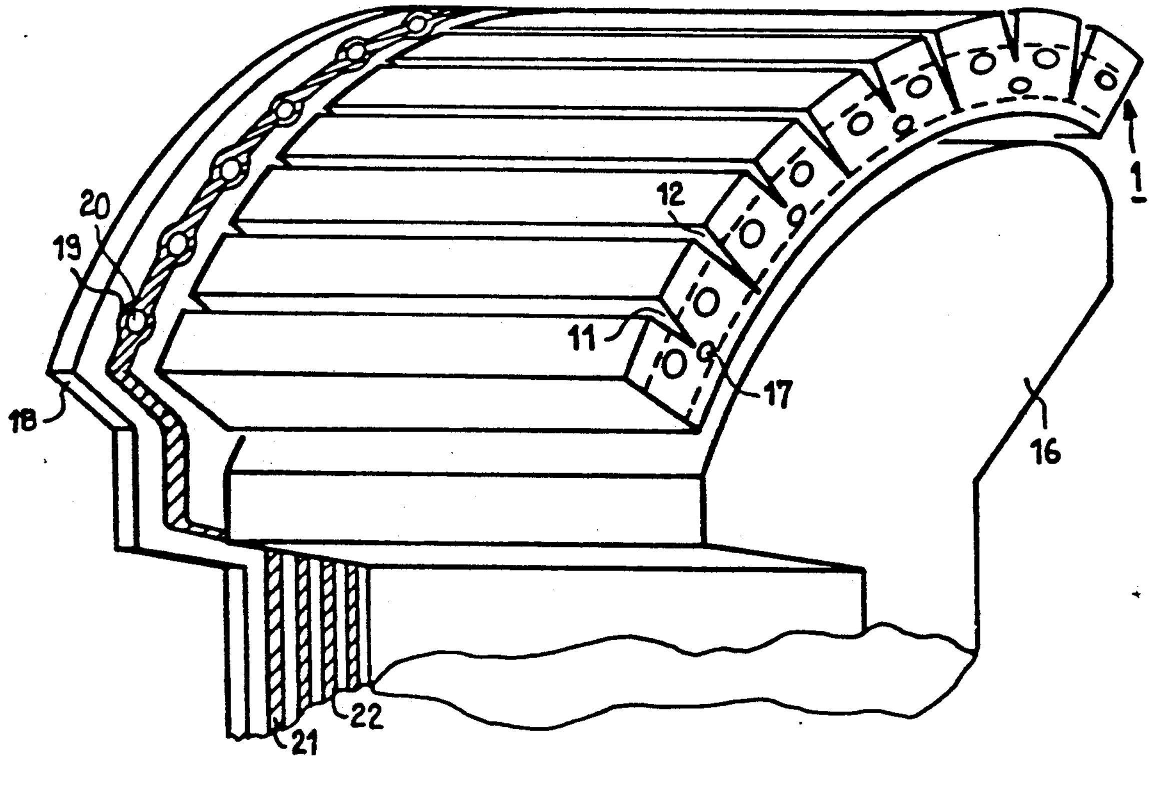
FIG. 2: the appearance of the above bar after deformation following a cycle of heating followed by a cooling.

The essential characteristic of the invention lies in the nature of the material forming the support 2. When the cutting operation is ended, even the deepest cuts 12 do not break its rigidity. The bar stays rectilinear and rigid: the material forming it is hard. However, this material has the particular feature of softening when it is heated, and of taking the shape imposed on it at this moment. Hence, an appropriate, curved form 13 is used, and the form 13 and the bar 1 are placed in an oven which is taken to an adequate temperature. Under the effect of its own weight or, possibly, by exerting an elastic force at its ends 14 and 15, the bar can be made to get curved according to the shape of the form 13. At the end of a period, judged by experiment to be sufficiently long, the oven is allowed to cool down. The bar then has the appearance shown schematically in FIG. 2: it is now rigid again but curved.

In an alternative embodiment, the thermoformable curved support is formed by the acoustic transition blade itself. During the partition of the bar, the sawing is done from the base 2 up to a certain height in the blade. In both cases it is subsequently possible, by making saw marks of appropriate width, to form convex or concave curved bars.

The material which can be used for the support 2 and which has the thermoforming properties thus revealed is preferably a polymerizable material which as the aspect of a foam before its polymerization. This foam may be syntactic, i.e. it may include a liquid with micro-bubbles of a gas, or it may be non-syntactic, i.e. it may be in the form of beads which get agglomerated with one another during polymerization. This foam is preferably an epoxy resin or else a polyurethane. It is preferably a cold polymerizable foam. To adapt the impedance of the support, there is provision for charging the foam with micro-beads, in particular with plastic micro-beads. In a preferred example, the plastic micro-beads are phenolic micro-beads. In practice, materials are chosen for which the thermoforming is obtained at a temperature of the order of or greater than 90°–100°. In effect, it is known that piezoelectric probes get heated during their use. They are then carried to temperatures which could, if care is not taken about it, cause undesired deformations in the bar. For this reason, the thermoforming temperature is chosen at the indicated value. At this temperature, in effect, the probes cannot be used on human bodies and there is therefore no risk that this temperature will be reached during an experiment.

To enable its thermoforming, it is necessary, as in the prior art, for the support 2 to be thin. In the invention, it has a thickness substantially equal to the elastic support of the prior art referred to. To then reinforce the rigidity of this support, it is solidly joined to a base 16. Then the thermoformed bar is placed at the bottom of a mold, with its concave part pointed upwards and, from the top, there is poured a material which is the same as that forming the support (but is not yet polymerized). Then the material of the base is polymerized. The mold is shaped so as to furthermore give this base a form useful for the manipulation of the probe. The base is made as soon as possible after the thermodeformation of the bar. For example, this operation is done on the next day. Since the material which forms the base is the same as the one forming the support, if these operations are properly done, at the end it is almost impossible to distinguish between the part, in the base-support, belonging to the support and that belonging to the base. There is therefore no longer any acoustic reflection surface beneath the support. The reflections can therefore no longer take place. The value of having chosen a cold polymerizable material can be easily understood. During the subsequent making of the base, it is not necessary to polymerize this base material to reheat the entire bar. This would risk destroying the deformation previously given to it.

The advantage of thermodeformable materials is that of further being capable of accepting great variety of charging materials. This gives them highly suitable for the accurate setting of the acoustic impedance.

To achieve the connection of the piezoelectric elements of the bar, it is possible to deposit micro-drops 17 of indium on the apparent lateral metallizations of the blocks of each element. Then, a printed circuit 18, provided with connecting tracks such as 21 and 22; is brought near to each side of the bar. This circuit has, facing the connections to be made, metallizations 19 which too are provided with indium micro-drops 20. Then, the printed circuits are laid against the flanks of the bar and, by a reflow operation in an oven, it is possible to obtain the connection of all the elements to the tracks. These tracks conduct the electrical signals, at transmission and reception, from the generating elements and towards the reception elements.

The shape presented up to now for the bar is a convex shape. However, there are known methods in the prior art for fabricating concave shapes. It is clear that a probe with a concave bar can be fabricated in the same way. The only precaution to be taken consists in making, in this case, cuts 10 and 11 which are wide enough so that, at the deformation to which the bar is subjected, the piezoelectric elements do not come into contact with one another. In this case, also, it is possible to make a base that intimately adheres to the support.

Obviously, numerous modifications and variations of the present invention are possible in light of the above teachings. It is therefore to be understood that within the scope of the appended claims, the invention may be practiced otherwise than as specifically described herein.

We claim:

1. Method for the fabrication of a bar probe, comprising the steps of:

bonding a piezoelectric bar to a thermodeformable supporting blade (2), making cuts (11, 12) enabling the making of independent piezoelectric transducers and/or the dividing of the piezoelectric transducers, heating and deforming the bar to give it the desired shape, by placing said supporting blade in contact with a curved mold so as to maintain the uniform thickness of said supporting blade.

2. A method according to claim 1, further comprising the steps of placing said bar in a mold, pouring material which is the same as a material forming said supporting blade thereover, and polymerizing the material to form a base.

3. A probe with a curved bar for echograph, comprising:

a deformable support made of a thermoformable cold polymerizable epoxy resin which is rigid at ambient temperature;

piezoelectric elements fixed to said support, said support and piezoelectric elements having the shape of a curved bar with said support having a uniform thickness; and a base fixed to said support, said base having the same shape and material as said support.

4. Probe according to claim 3, wherein the material is a polyurethane.

5. Probe according to any one of claims 3 or 4, wherein the material is a foam.

6. Probe according to claim 5, wherein the foam comprises plastic micro-beads.

7. Probe according to claim 6, wherein the microbeads are phenolic.

8. Probe according to any one of claims 3 or 4, wherein the bar is convex curved.

9. Prove according to any one of claims 3 or 4, wherein the bar is curved and concave.

10. The probe according to claim 3, wherein said base is formed by pouring said material into a mold containing said support and polymerizing the same without adding heat to said support.

* * * * *